(12) United States Patent
Libon et al.

(10) Patent No.: US 7,033,591 B1
(45) Date of Patent: Apr. 25, 2006

(54) IMMUNOSTIMULANT BACTERIAL MEMBRANE FRACTIONS IN CANCER TREATMENT

(75) Inventors: Christine Libon, Saint Julien en Genevois (FR); Nathalie Corvaia, Saint Julien en Genevois (FR); Alain Beck, Collonges sous Saleve (FR); Jean-Yves Bonnefoy, Le Sappey (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 09/936,677

(22) PCT Filed: Mar. 15, 2000

(86) PCT No.: PCT/FR00/00623

§ 371 (c)(1),
(2), (4) Date: Sep. 14, 2001

(87) PCT Pub. No.: WO00/54790

PCT Pub. Date: Sep. 21, 2000

(30) Foreign Application Priority Data

Mar. 15, 1999 (FR) .................................. 99 03154

(51) Int. Cl.
  *A61K 39/00* (2006.01)
  *A61K 39/02* (2006.01)
  *A61K 39/108* (2006.01)
  *A61K 45/00* (2006.01)

(52) U.S. Cl. ............................... 424/184.1; 424/234.1; 424/259.1; 424/278.1

(58) Field of Classification Search ............ 424/184.1, 424/234.1, 259.1, 278.1, 178.1, 94.61, 186.1; 435/69.1, 325, 287.9, 6, 344, 252.3; 536/23.5; 530/395

See application file for complete search history.

(56) References Cited

U.S. PATENT DOCUMENTS

| 4,501,693 A | * | 2/1985 | Dussourd d'Hinterland et al. ............................................... 435/71.2 |
| 5,242,806 A | * | 9/1993 | Yen-Maguire et al. ........ 435/32 |
| 5,648,478 A | * | 7/1997 | Henderson ................. 536/24.1 |
| 5,674,739 A | * | 10/1997 | Shyjan .................... 435/252.3 |
| 5,776,898 A | * | 7/1998 | Teicher et al. ................. 514/6 |

FOREIGN PATENT DOCUMENTS

FR  2596064  * 9/1986

OTHER PUBLICATIONS

Cheng et al (IEEE Transactions on Medical Imaging, vol. 17, No. 3, pp 442-450, Jun. 1998).*
Burton, R.C. 2000. Malignant melanoma in the year 2000. CA Cancer J. Clin. 50:209-213.*

* cited by examiner

*Primary Examiner*—Mark Navarro
(74) *Attorney, Agent, or Firm*—Hueschen and Sage (57) ABSTRACT

The invention concerns the use of a membrane fraction of gram-negative bacteria, in particular *Klebsiella pnemoniae* for preparing a pharmaceutical composition that is immunostimulant and/or capable of inducing an antitumoral immune response, designed in particular for treating and preventing cancers. The invention further comprises methods for preparing said membrane factions and pharmaceutical compositions containing them, in particular combined with anticancer compounds.

16 Claims, 2 Drawing Sheets

IMMUNOSTIMULANT BACTERIAL MEMBRANE FRACTIONS IN CANCER TREATMENT

The present invention relates to the use of a membrane fraction of Gram-negative bacteria, in particular of *Klebsiella pneumoniae*, for preparing a pharmaceutical composition which is immunostimulant and/or capable of inducing an antitumor immune response and which is intended, in particular, for treating and preventing cancers. The invention also comprises methods for preparing said membrane fractions and also pharmaceutical compositions containing them, in particular combined with anticancer compounds.

The transformation of a normal cell into a malignant cell is the result of many different events which may occur spontaneously, such as mutations or gene rearrangements, or be induced by chemical, physical or viral agents.

Tumors are infiltrated by immunocompetent cells, in particular lymphocytes, dendritic cells and macrophages.

Tumor-associated macrophages (TAMs) originate from the blood circulation and are recruited to the tumor site by cytokines. TAMs bind to the tumor cells via glycoproteins, sugars and phospholipids and proliferate at the tumor site (J. Natl. Cancer Inst., 1998, 90:1583). There, they secrete many cytokines which contribute to their antitumor activity. Among the most important are TNF-α and IL-12.

The antitumor activity of TNF-α has been demonstrated in experimental models in mice (Beyaert R. and Fiers W., Cytokines, chapter 24, 335–360 Academic Press. 1998) and has been tested in humans for treating bladder cancers: alone, it has moderate activity (Steinberg et al., Ann. Oncol., 1992, 3,741–745; Eur. Urol. 1992, 22:112).

The production of IL-12 by activated macrophages serves to modulate the immune response by promoting the formation of Th1-type CD4+ T lymphocytes which produce IL-2 and IFN-γ. The inhibitory activity of IL-12 on angiogenesis and tumor regression is well known and appears to be linked to the induction of IFN-γ, which stimulates the production of IP-10 (interferon-inducible protein-10) and of MIG (monokine induced by IFN-γ) (J. Natl. Cancer Inst., 1998, 90:1583).

BCG (Bacille Calmette Guérin) therapy is used to prevent the recurrence of certain types of bladder cancer. The mechanism of action currently proposed is based on the production of cytokines: early release of inflammatory cytokines (TNF-α, IL-1, IL-6, IL-8) and, secondly, production of IL-2 and of IFN-γ (Th1 response), then later of IL-4, of IL-5 and of IL-10 (Th2 response). Finally, there occurs a phase of cell activation with amplification of cytotoxic populations (Patard et al., Progrès en Urologie, 1998, 8,415–421).

However, BCG therapy does not only have advantages, since the effectiveness sometimes observed is at the expense of a morbidity which is also greater. In addition, there are contraindications for BCG therapy: active tuberculosis (but not prior tuberculosis), immunosuppression (HIV, transplantation, etc.), prior systemic reaction to BCG (hepatitis, pneumonia, BCGitis), steroid treatments. Furthermore, resistances or recurrences exist after BCG therapy.

The membrane fraction of *K. pneumoniae* I145 goes into the composition of a pharmaceutical preparation which prevents the occurrence and recurrence of respiratory infections of bacterial origin and which has been used in humans for 20 years. For this reason, there has been enough time to assess the nontoxicity of the product. The set of data cited above shows that there exists, today, a need to have novel immunostimulants free of toxic activity. Such immunostimulants would be of great value for treating certain types of cancer.

Surprisingly, the authors of the present invention have demonstrated that membrane fractions of a Gram-negative bacterium, especially *Klebsiella pneumoniae* (named FMKp), in particular membrane fractions obtained using the methods as described hereinafter in the examples, have the desired immunostimulant properties.

The inventors have shown, surprisingly, that the FMKp or one of its major constituents, the OmpA outer membrane protein named P40 (as described in patent applications WO 95/27787 and WO 96/14415) is capable not only of stimulating the proliferation of human blood mononucleated cells, thus demonstrating its immunostimulant activity, but also of inducing, in particular by monocytes, the production of TNF-α and of IL-12, which are cytokines involved in the antitumor immune response.

Thus, the subject of the present invention is the use of a membrane fraction of Gram-negative bacteria, in particular of *Klebsiella pneumoniae*, as a compound which is immunostimulant and/or capable of inducing an antitumor immune response, or for preparing a pharmaceutical composition which is immunostimulant and/or capable of inducing an antitumor immune response, this being whatever the mode of administration in vivo chosen (enteral or parenteral route).

In the present invention, the term "immunostimulant compound" or "immunostimulant pharmaceutical composition" is intended to denote a compound, or a pharmaceutical composition, capable of increasing a nonspecific immune response.

In the present invention, the expression "compound capable of inducing an antitumor immune response" or "pharmaceutical composition capable of inducing an antitumor immune response" is intended to denote a compound, or a pharmaceutical composition, capable, in particular, of increasing the effectiveness of an anticancer compound or increasing the effectiveness of an anticancer treatment, such as for example treatment by radiotherapy.

The invention also relates to the use as claimed in the invention, characterized in that the membrane fraction comprises at least membrane fractions of two different strains of bacteria.

In the present invention, the expression "membrane fraction of a bacterium" is intended to denote any purified or partially purified membrane fraction or extract which is obtained from a culture of said bacterium and for which the method of preparation comprises at least one step for lysing the bacteria obtained after culturing and one step for separating the fraction containing the membranes of said bacteria from the total lysate obtained after the lysis step, in particular by centrifugation or filtration.

In the present invention, the expression "membrane fraction of a bacterium when said bacterium is *Klebsiella pneumoniae*" is also intended to denote the P40 protein, which is the active fraction of the membrane fraction of *Klebsiella pneumoniae*, of amino acid sequence SEQ ID No. 2, or a fragment thereof.

According to the invention, the membrane fractions may be prepared according to the methods known to those skilled in the art, such as for example the method described by Haeuw J. P. et al. (Eur. J. Biochem, 255, 446–454, 1998).

According to one particular embodiment, the invention relates to a use as claimed in the invention, characterized in that the membrane fraction is prepared using a method comprising the following steps:
a) culturing of said bacteria in a culture medium which allows their growth, followed by centrifugation of said culture;
b) where appropriate, deactivation of the lytic enzymes of the bacterial pellet obtained in step a), then centrifugation of the suspension obtained;
c) extraction and elimination of the non-membrane-bound proteins and of the nucleic acids of the pellet obtained in step a) or b) with at least one cycle of washing the pellet in an extraction solution;
d) digestion of the membrane pellet obtained in step c) in the presence of proteolytic enzymes, followed by centrifugation;
e) at least one cycle of washing the pellet obtained in step d) in a physiological solution and/or in distilled water; and
f) ultrasonication of the pellet obtained in step e).

Step b) for deactivating the lytic enzymes of the bacterial pellet obtained in step a) may be carried out using any known method for deactivating enzymes, such as, in particular, by heating the resuspended bacterial pellet to a temperature preferably close to 100° C., or by adding an inhibitor of the activity of these enzymes.

Step c) for extracting and eliminating the non-membrane-bound proteins and the nucleic acids of the pellet obtained in step a) or b) may be carried out, for example, with at least one cycle of washing the pellet in an extraction solution corresponding to the addition of a hypertonic solution (extraction solution), preferably a saline solution with a molarity close to 1 M, followed, after a period of contact sufficient for the desired effect, by centrifugation of the suspension obtained and elimination of the supernatant obtained after said centrifugation, this washing cycle possibly being reproduced several times.

Step d) for digesting the membrane pellet obtained in step c) may be carried out in the presence of a solution of proteolytic enzymes, such as for example trypsin, chymotrypsin or any known enzyme with proteolytic activity, the conditions of the reaction, pH of the solution, and temperature and duration of the reaction preferably being adjusted to the optimal conditions for the activity of the enzyme(s) chosen, followed by a centrifugation, this digestion cycle possibly being reproduced several times with the same enzyme or the same combination of enzymes, or with a different enzyme for each digestion cycle carried out.

Step e) for washing the pellet obtained in step d) is carried out by taking the pellet up in in [sic] a physiological solution or in distilled water, followed, after a sufficient period of contact, by a centrifugation, this washing cycle possibly being reproduced several times.

Finally, the objective of step f) for ultrasonicating the pellet is, in particular, to disintegrate and homogenize the membrane fraction obtained at the end of step e). The ultrasonication conditions (duration and power) will be determined by those skilled in the art depending, for example, on the amount of membrane fraction to be treated.

According to another particular embodiment, the invention relates to a use as claimed in the invention, characterized in that the membrane fraction is prepared using a method comprising the following steps:
a) culturing of said bacteria in a culture medium which allows their growth, followed, where appropriate, by centrifugation;
b) freezing of the culture medium or of the pellet obtained in step a), followed by thawing and drying of the cells;
c) elimination, using a DNase, of the nucleic acids from the dried cells obtained in step b), which have been resuspended;
d) grinding of the cells obtained in step c) and clarification of the suspension obtained;
e) precipitation, in acid medium, of the suspension obtained in step d) and elimination of the pellet;
f) neutralization of the supernatant obtained in step e) containing the membrane suspension, followed by dialysis and concentration of the membrane suspension; and
g) sterilization of the concentrated membrane suspension obtained in step f).

The conditions for freezing in step b) of the method below [sic] will, of course, be determined by those skilled in the art depending on the initial amount of pellet to be treated, preferably carried out at 4° C. for at least 48 hours for the equivalent of 1 kg of dried cells.

In step c), the nucleic acids are eliminated, for example, by adding a DNase at a final concentration of 5 mg/ml of a suspension of cells at a concentration equivalent to 5% of dried cells.

The grinding of the cells obtained in step c) may be carried out using any system or apparatus known to those skilled in the art for grinding cells, such as presses or preferably such as Manton Gaulinet loop grinding for 30 minutes.

The clarification of the suspension obtained after grinding may be carried out using any system or apparatus known to those skilled in the art for clarifying ground bacterial cell material, such as the Sharpless [sic] system.

Step e) for precipitating, in acid medium, the suspension obtained in step d) may be carried out, for example, with acetic acid. The precipitation is followed by elimination of the pellet using, for example, a system of the Sharpless type and by recovery of the supernatant.

Step f) consists of a step in which the supernatant, obtained after precipitation in acid medium, is neutralized, diluted, dialyzed and then concentrated.

Finally, the last step consists of a step for sterilizing the membrane fraction concentrate obtained in the preceding step, for instance by heating at 121° C. for approximately 35 minutes, for example.

The invention relates particularly to the use as claimed in the invention, characterized in that the membrane fraction is the *Klebsiella pneumoniae* P40 protein of sequence SEQ ID No. 2, or a fragment thereof.

The expression "fragment of P40 protein" is intended to denote, in particular, any fragment of amino acid sequence included in the amino acid sequence of the P40 protein, which is capable of increasing a nonspecific immune response and/or capable of inducing an antitumor immune response, and which comprises at least 5 amino acids, preferably at least 10 amino acids, or more preferably at least 15 amino acids.

Of course, said P40 protein, or fragments thereof, may be obtained by chemical synthesis or in the form of recombinant peptides.

The methods for preparing recombinant peptides are, today, well known to those skilled in the art and will not be developed in the present description. Among the cells which may be used for producing these recombinant peptides, mention should, of course, be made of bacterial cells (Olins P. O. and Lee S. C., 1993, Recent advances in heterologous gene expression in *E. coli*. Curr. Op. Biotechnology 4:520–525), but also yeast cells (Buckholz R. G., 1993, Yeast Systems for the Expression of Heterologous Gene Products. Curr. Op. Biotechnology 4:538–542), as well as animal cells, in particular mammalian cell cultures (Edwards C. P. and Aruffo A., 1993, Current applications of COS cell based transient expression systems. Curr. Op. Biotechnology 4, 558–563), but also insect cells in which methods implementing, for example, baculoviruses may be used (Luckow V. A., 1993, Baculovirus systems for the expression of human gene products. Curr. Op. Biotechnology 4, 564–572).

A subject of the invention is also the use as claimed in the invention, characterized in that the pharmaceutical composition also comprises an agent for vehiculing said membrane fraction in a form which makes it possible to improve its stability and/or its immunostimulant activity and/or its capacity to induce an antitumor immune response, such as in the form of an emulsion of the oil-in-water or water-in-oil type, or in the form of a particle of the liposome, microsphere or nanosphere type, or any type of structure which enables said membrane fraction to be encapsulated and presented in particulate form.

Also included in the present invention is the use as claimed in the invention, characterized in that the pharmaceutical composition also comprises an agent for potentiating the immunostimulant activity and/or the antitumor immune response of said membrane fractions.

Among said agents for potentiating the immunostimulant activity and/or the antitumor immune response of said membrane fractions, cytokines and cellular compounds are preferred.

Among cytokines, mention may be made, without being limited thereto, of: IL-2, IL-12, IL-18, IFN-γ and IFN-α.

Among cellular compounds, nucleic acids, compounds of the ribosome family or proteins of the heat-shock protein family are in particular preferred.

Also included in the present invention is the use as claimed in the invention, characterized in that the pharmaceutical composition also comprises a potentiating agent which makes it possible to regulate the immunostimulant activity and/or the antitumor immune response of said membrane fractions.

Among said potentiating agents which make it possible to regulate the immunostimulant activity and/or the antitumor immune response of said membrane fractions, hormones and growth factors are preferred.

Among hormones, mention may be made, but without being limited thereto, of β-hCG.

Among growth factors, mention may be made, but without being limited thereto, of: EGF, IGF-1, IGF-2, GM-CSF and G-CSF.

The subject of the invention is also the use as claimed in the invention, for preparing a pharmaceutical composition intended to be administered in combination with an anticancer treatment, in particular an anticancer treatment by chemotherapy (mono- or polychemotherapy) and/or radiotherapy.

According to the invention, the preparation of the pharmaceutical composition is intended to be administered via the enteral or parenteral route, and simultaneously with, separately from or spread out over time with the anticancer treatment.

The invention also comprises the use as claimed in the invention, for preparing a pharmaceutical composition comprising a compound with anticancer activity combined with said membrane fraction.

Many compounds with anticancer activity may thus be combined with said membrane fraction which is immunostimulant and/or capable of inducing an antitumor immune response.

Among these compounds, mention may in particular be made, but without being limited thereto, of protease inhibitors or compounds with anti-angiogenic activity, such as for example:

protease inhibitors such as TIMPs;

or the following compounds with anti-angiogenic activity: angiostatin, endostatin, MCP-1, IP-10 and PF-4, and also anti-VEGF, anti-angiogenin, anti-aFGF and anti-bFGF antibodies, antisense sequences or peptides.

Thus, the invention relates to the use as claimed in the invention, characterized in that said combined anticancer treatment is a chemotherapeutic treatment comprising a protease inhibitor or a compound with anti-angiogenic activity.

The subject of the invention is also the use as claimed in the invention, for preparing a pharmaceutical composition intended to prevent or treat cancers, in particular bladder cancers, prostate cancers, colon cancers, liver cancers or malignant melanomas.

In another aspect, the invention relates to a method for preparing a membrane fraction of Gram-negative bacteria, in particular *Klebsiella pneumoniae*, characterized in that it comprises the following steps:

a) culturing of said bacteria in a culture medium which allows their growth, followed by centrifugation of said culture;

b) where appropriate, deactivation of the lytic enzymes of the bacterial pellet obtained in step a), then centrifugation of the suspension obtained;

c) extraction and elimination of the non-membrane-bound proteins and of the nucleic acids of the pellet obtained in step a) or b) with at least one cycle of washing the pellet in an extraction solution;

d) digestion of the membrane pellet obtained in step c) in the presence of protease enzymes, followed by centrifugation;

e) at least one cycle of washing the pellet obtained in step d) in a physiological solution and/or in distilled water; and f) ultrasonication of the pellet obtained in step e).

The invention also comprises the method for preparing a membrane fraction of Gram-negative bacteria, in particular *Klebsiella pneumoniae*, characterized in that it comprises the following steps:

a) culturing of said bacteria in a culture medium which allows their growth, followed, where appropriate, by centrifugation;

b) freezing of the culture medium or of the pellet obtained in step a), followed by thawing and drying of the cells;

c) elimination, using a DNase, of the nucleic acids from the dried cells obtained in step b), which have been resuspended;

d) grinding of the cells obtained in step c) and clarification of the suspension obtained;

e) precipitation, in acid medium, of the suspension obtained in step d) and elimination of the pellet;

f) neutralization of the supernatant obtained in step e) containing the membrane suspension, followed by dialysis and concentration of the membrane suspension; and g) sterilization of the concentrated membrane suspension obtained in step f).

The membrane fractions which can be obtained using said methods of course form part of the invention.

The titer of proteoglycan of the membrane fractions which can be obtained using said methods, which proteoglycan is the active principle of the FMKp, which titer is represented by the sum of the galactose and protein contents, is preferably:

for the galactose: between 1.2 g/l and 3.4 g/l;
for the proteins: between 7.5 g/l and 14.9 g/l.
More preferably, this titer will be:
for the galactose: between 1.8 g/l and 2.6 g/l;
for the proteins: between 9.3 g/l and 11.7 g/l.

The invention also relates to the pharmaceutical compositions comprising a membrane fraction which can be obtained using the methods as claimed in the invention.

Also included in the present invention are the pharmaceutical compositions comprising a membrane fraction of a Gram-negative bacterium, in particular of *Klebsiella pneumoniae*, characterized in that it is combined with an anticancer treatment by chemotherapy and/or by radiotherapy.

The term "membrane fraction" is herein intended to denote any membrane fraction of the Gram-negative bacterium as defined above, including that which can be obtained using the methods as claimed in the invention and the P40 protein or a fragment thereof.

Preferably, the invention relates to a pharmaceutical composition as claimed in the invention, characterized in that it contains an anticancer compound as a combination product for use which is simultaneous, separate or spread out over time, in particular an anticancer compound chosen from protease inhibitors or from compounds having anti-angiogenic activity.

Preferably, said pharmaceutical compositions as claimed in the invention may also comprise agents such as vehicles, agents capable of potentiating and/or of regulating the immunostimulant activity and/or the antitumor immune response of said membrane fractions as defined above.

The legends to the figures and examples which follow are intended to illustrate the invention without in any way limiting the scope thereof.

LEGENDS TO THE FIGURES

The mononucleated cells (PBMC) are obtained by separation with the aid of a solution of Ficoll-sodium metrizoate, using total blood. The PBMC are then seeded in a proportion of 10 000 cells/well in the presence of stimulating agents, in a total volume of 200 µl. After incubation for 72 h. the proliferation is objectified by adding tritiated thymidine. The results are expressed as stimulation index=[cpm PBMC+stimulus]/[cpm PBMC without stimulus (=RPMI medium+10% SVP)].

The monocytes are cultured in RPMI 1640 medium +10% SVF and in the presence of various concentrations of product. The cells are incubated in an incubator at 37° C. in an atmosphere containing 5% of $CO_2$. Culture conditions: 200 000 cells/well, incubation for 18 h. After incubation, the culture plates are centrifuged and the supernatants are aliquoted and stored at −80° C. until they are assayed. The concentrations of cytokines present in the culture supernatants are determined by ELISA (Enzyme-Linked ImmunoSorbent Assay) Predicta kit from Genzyme (detection threshold at 3 pg/ml).

The monocytes are cultured in RPMI 1640 medium+10% SVF and in the presence of various concentrations of product. The cells are incubated in an incubator at 37° C. in an atmosphere containing 5% of $CO_2$. Culture conditions: 500 000 cells/well, incubation for 24 h. After incubation, the culture plates are centrifuged and the supernatants are aliquoted and stored at −80° C. until they are assayed. The concentrations of cytokines present in the culture supernatants are determined by ELISA: Endogen antibody pair (detection threshold at 15 pg/ml.)

EXAMPLE 1

Production of the Membrane Fraction of *K. pneumoniae* (FMKp)

Method No. 1

The extraction of the *K. pneumoniae* I145 membranes from the centrifugation pellet from the step is preferably preceded by a step for destroying the lytic enzymes of the cellular components contained in the pellet, for example by heating the pellet to 100° C., optionally after redissolving it.

The actual extraction of the membranes from the centrifugation pellet is preferably carried out by treating the cellular components of the pellet, after optional destruction of the lytic enzymes, with a saline solution, for example 1M sodium chloride, one or more times, then centrifuging the suspension obtained, preferably at 20 000 g; the supernatant from this centrifugation, which is eliminated, contains the nonmembrane impurities such as proteins and nucleic acids, while the pellet contains the membranes.

After separation of the saline solution containing the impurities, the membranes are digested in the presence of proteolytic enzymes, preferably trypsin and chymotrypsin, in solution at pH 8, at 37° C. for 4 hours.

After digestion, the solution is homogenized by ultrasonication. The product thus obtained constitutes the membrane fraction named FMKp.

The supernatant obtained is centrifuged again under the same conditions, preferably at 140 000 g.

Preparation of the Membrane-Bound Glycopeptides

This fraction is prepared from the pellet obtained by centrifugation at 40 000 g for 20 minutes. Said pellet is resuspended in physiological saline and then this suspension is brought to 100° C. for 10 minutes in a waterbath of boiling water so as to deactivate the lytic enzymes. After cooling, the suspension is centrifuged for 30 min at 20 000 g. The pellet obtained is extracted twice with 1 M NaCl in order to eliminate the proteins and the nucleic acids. The membranes are recovered by centrifugation for 30 minutes at 20 000 g.

They are then subjected to digestion by trypsin at pH 8 and at 37° C. for 4 hours, then by chymotrypsin under the same conditions.

The membranes are then recovered by centrifugation at 2 000 g for 30 minutes, washed with physiological saline and then distilled water and subjected to 15-minute disintegration by ultrasound.

Method No. 2

After thawing at +4° C. for a minimum of 48 h, 1 kg of dry *K. pneumoniae* cells is resuspended at 5% dry cells. DNase is added at 5 mg/l. Next, Manton Gaulin loop grinding is carried out for 30 min, followed by a clarification of a Sharples at 50 l/h, and then precipitation with acetic acid at pH=4.2+0.1 for 30 min. The pellet is eliminated (Sharples at 25 l/h) and the supernatant is neutralized and diluted to twice the initial volume with osmosed water. Dialysis at constant volume is then performed on PUF 100 up to 800 Ωcm, followed by concentration of the membrane suspension (MS) thus obtained, to 11 l/kg of dry cells. The MS is then autoclaved at +121° C. for 35 min and can be stored at +4° C. for 6 weeks.

Characteristics of the FMKp

By definition, the titer of proteoglycan, which is the active principle of the FMKp, is equal to the sum of the galactose and protein contents, galactose: on average 2.2 g/l
proteins: on average 10.5 g/l

EXAMPLE 2

Proliferation of PBMC from Human Blood

Figure 1:
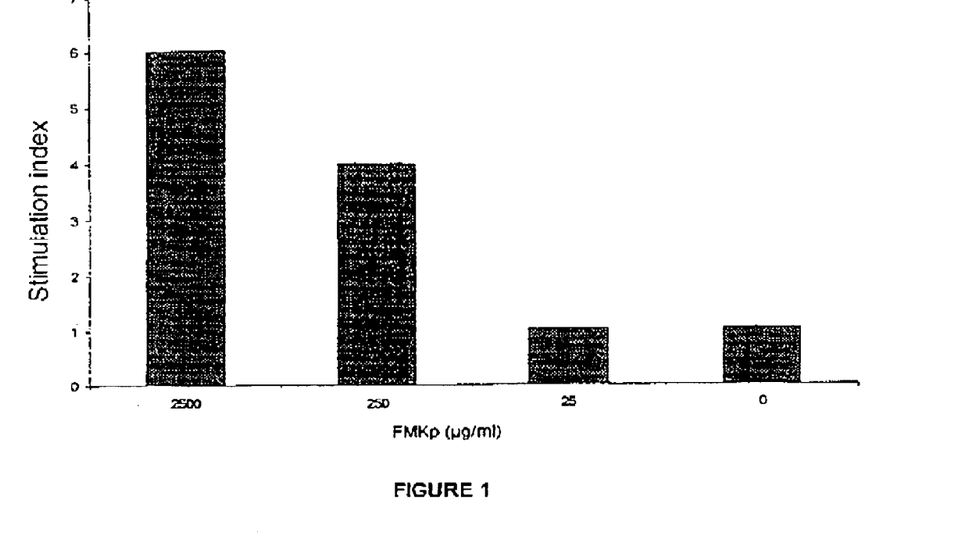
FIG. 1: Proliferation of PBMC in the presence of FMKp—Dose-response study
Figure 2:
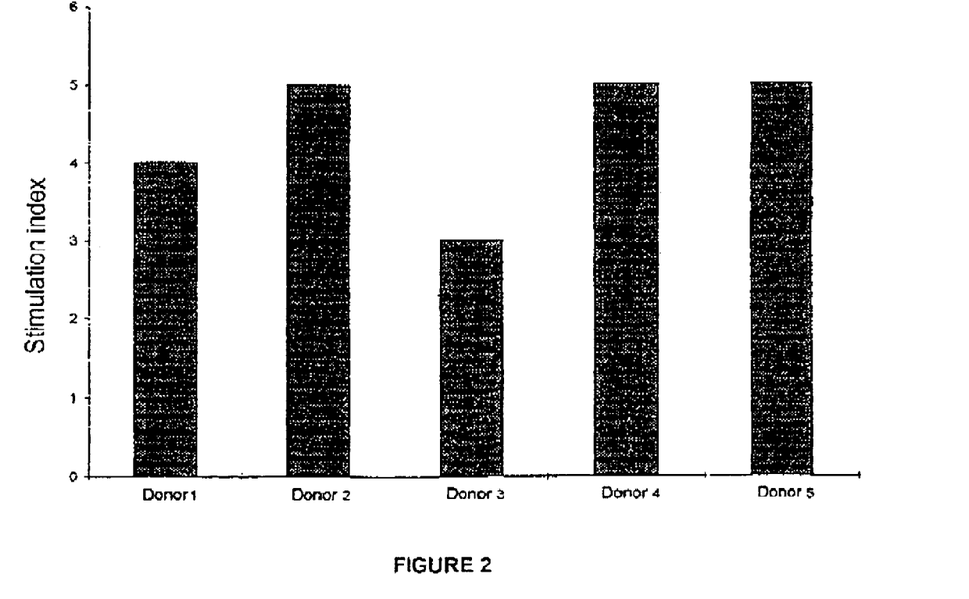
FIG. 2: Proliferation of PBMC in the presence of FMKp—Reproducibility of the effect on several donors (FMKp at 250 µg/ml).

The results obtained show that, surprisingly, the FMKp triggers PBMC proliferation. This effect is dose-dependent and maximal for 2.5 mg/ml of FMKp (FIG. 1). Moreover, this effect is reproducible (FIG. 2).

EXAMPLE 3

Production of Cytokines by Monocytes Purified from Human Blood

Human monocytes are obtained from the mononucleated cells (lymphocytes, monocytes, NK cells, etc.) isolated beforehand from total human blood. The production of monocytes is based on the expression, in large amount, of the CD14 surface antigen on the cells. The separation is a positive selection. The effectiveness of the magnetic separation of the monocytes is then evaluated by flow cytometry, labeling with a fluorescein isothiocyanate (FITC)—coupled CD13 antibody: the cell suspension then contains 94 to 97% of monocytes.

Figure 3:
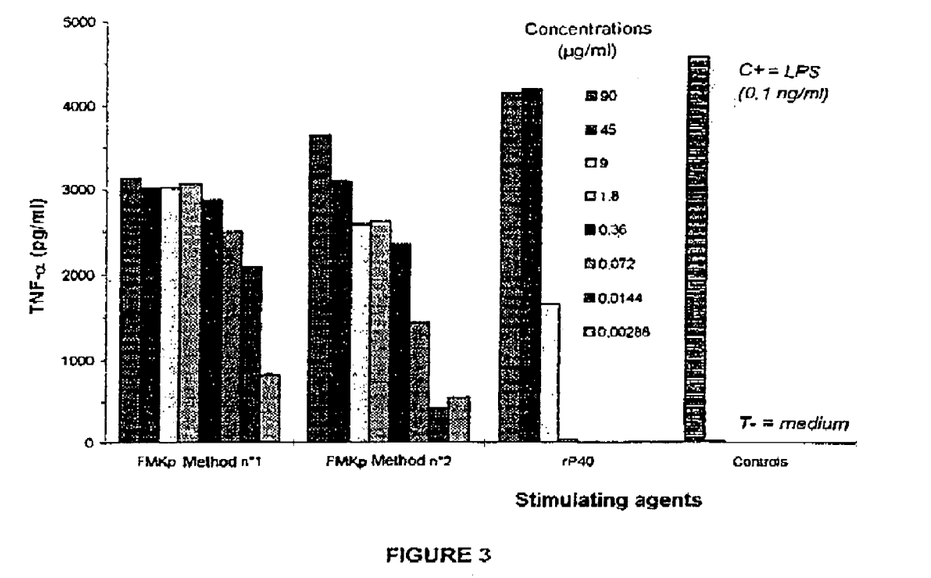
FIG. 3: Production of TNF-α by blood monocytes
Figure 4:
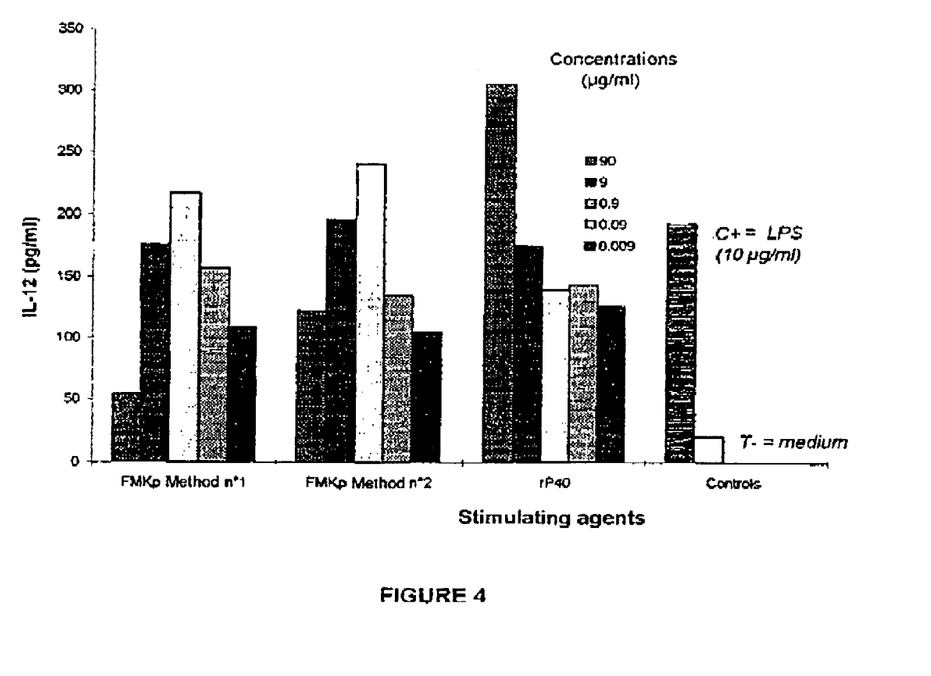
FIG. 4: Production of IL-12 p70 (biologically active) by blood monocytes.

The results from in vitro studies demonstrate that, interestingly, the FMKp is an immunostimulant which induces the proliferation of PBMC from human blood with a direct effect on the monocytes: production of TNF-α (FIG. 3) and of IL-12 p70 (FIG. 4). It is noteworthy that the recombinant P40 protein (rP40), the OmpA of *K. pneumoniae*, is also capable of stimulating the production of TNP-α (FIG. 3) and of IL-12 p70 (FIG. 4) by human monocytes.

The invention claimed is:

1. A method of stimulating an immune response and/or inducing an antitumor immune response in a mammal, including a human, in need thereof, characterized by stimulation of proliferation of peripheral blood mononuclear cells, whereby a membrane fraction of Gram-negative bacteria, comprising proteoglycans with a proteoglycan content of between 8.7 g/L and 18.3 g/L, is administered in the form of a pharmaceutical composition in combination with an anticancer treatment in an amount effective to result in such induction and or stimulation.

2. The method of claim 1, wherein the anticancer treatment is chemotherapy and/or radiotherapy.

3. The method of claim 1, wherein the pharmaceutical composition is administered simultaneously with, separately from, or at intervals with, the anticancer treatment.

4. The method of claim 3, wherein the pharmaceutical composition is administered enterally or parenterally.

5. The method of claim 1, wherein the combined anticancer treatment is a chemotherapeutic treatment comprising a protease inhibitor or a compound with anti-angiogenic activity.

6. The method of claim 1, for treating cancers.

7. The method of claim 6, for treating bladder cancers, prostate cancers, colon cancers, liver cancers and malignant melanomas.

8. A pharmaceutical composition comprising a membrane fraction of Gram-negative bacteria, comprising proteoglycans with a proteoglycan content of between 8.7 g/L and 18.3 g/L, administered in combination with an anticancer treatment in an amount effective to stimulate an immune response and/or induce an antitumor immune response in a mammal, including a human, in need thereof, characterized by stimulation of proliferation of peripheral blood mononuclear cells.

9. The pharmaceutical composition of claim 8, which is combined with an anticancer treatment by chemotherapy and/or by radiotherapy.

10. The pharmaceutical composition of claim 9, which contains an anticancer compound as a combination product for use which is simultaneous, separate, or at intervals.

11. The pharmaceutical composition of claim 10, wherein the anticancer compound is chosen from protease inhibitors or from compounds with anti-angiogenic activity.

12. The method of claim 1, wherein the Gram-negative bacterium is Klebsiella pneumoniae.

13. The pharmaceutical composition of claim 9, wherein the chemotherapy is chosen from protease inhibitors or from compounds with anti-angiogenic activity.

14. The pharmaceutical composition of claim 8, wherein the Gram-negative bacterium is *Klebsiella pneumoniae*.

15. The method of claim 1, wherein the proteoglycan content is between 11.1 g/L and 14.3 g/L.

16. The pharmaceutical composition of claim 8, wherein the proteoglycan content is between 11.1 g/L and 14.3 g/L.

* * * * *

SEQUENCE LISTING

```
<160> NUMBER OF SEQ ID NOS: 4

<210> SEQ ID NO 1
<211> LENGTH: 1035
<212> TYPE: DNA
<213> ORGANISM: Klebsiella pneumoniae
<220> FEATURE:
<221> NAME/KEY: exon
<222> LOCATION: (1)..(1032)
<221> NAME/KEY: intron
<222> LOCATION: (1033)..(1035)
<221> NAME/KEY: CDS
<222> LOCATION: (1)..(1032)

<400> SEQUENCE: 1 atg aaa gca att ttc gta ctg aat gcg gct ccg aaa gat aac acc tgg      48
Met Lys Ala Ile Phe Val Leu Asn Ala Ala Pro Lys Asp Asn Thr Trp
 1               5                  10                  15 tat gca ggt ggt aaa ctg ggt tgg tcc cag tat cac gac acc ggt ttc      96
Tyr Ala Gly Gly Lys Leu Gly Trp Ser Gln Tyr His Asp Thr Gly Phe
             20                  25                  30 tac ggt aac ggt ttc cag aac aac aac ggt ccg acc cgt aac gat cag     144
Tyr Gly Asn Gly Phe Gln Asn Asn Asn Gly Pro Thr Arg Asn Asp Gln
         35                  40                  45 ctt ggt gct ggt gcg ttc ggt ggt tac cag gtt aac ccg tac ctc ggt     192
Leu Gly Ala Gly Ala Phe Gly Gly Tyr Gln Val Asn Pro Tyr Leu Gly
     50                  55                  60 ttc gaa atg ggt tat gac tgg ctg ggc cgt atg gca tat aaa ggc agc     240
Phe Glu Met Gly Tyr Asp Trp Leu Gly Arg Met Ala Tyr Lys Gly Ser
 65                  70                  75                  80 gtt gac aac ggt gct ttc aaa gct cag ggc gtt cag ctg acc gct aaa     288
Val Asp Asn Gly Ala Phe Lys Ala Gln Gly Val Gln Leu Thr Ala Lys
                 85                  90                  95 ctg ggt tac ccg atc act gac gat ctg gac atc tac acc cgt ctg ggc     336
```

```
                Leu Gly Tyr Pro Ile Thr Asp Asp Leu Asp Ile Tyr Thr Arg Leu Gly
                            100                 105                 110 ggc atg gtt tgg cgc gct gac tcc aaa ggc aac tac gct tct acc ggc          384
Gly Met Val Trp Arg Ala Asp Ser Lys Gly Asn Tyr Ala Ser Thr Gly
            115                 120                 125 gtt tcc cgt agc gaa cac gac act ggc gtt tcc cca gta ttt gct ggc          432
Val Ser Arg Ser Glu His Asp Thr Gly Val Ser Pro Val Phe Ala Gly
130                 135                 140 ggc gta gag tgg gct gtt act cgt gac atc gct acc cgt ctg gaa tac          480
Gly Val Glu Trp Ala Val Thr Arg Asp Ile Ala Thr Arg Leu Glu Tyr
145                 150                 155                 160 cag tgg gtt aac aac atc ggc gac gcg ggc act gtg ggt acc cgt cct          528
Gln Trp Val Asn Asn Ile Gly Asp Ala Gly Thr Val Gly Thr Arg Pro
                165                 170                 175 gat aac ggc atg ctg agc ctg ggc gtt tcc tac cgc ttc ggt cag gaa          576
Asp Asn Gly Met Leu Ser Leu Gly Val Ser Tyr Arg Phe Gly Gln Glu
            180                 185                 190 gat gct gca ccg gtt gtt gct ccg gct ccg gct ccg gct ccg gaa gtg          624
Asp Ala Ala Pro Val Val Ala Pro Ala Pro Ala Pro Ala Pro Glu Val
        195                 200                 205 gct acc aag cac ttc acc ctg aag tct gac gtt ctg ttc aac ttc aac          672
Ala Thr Lys His Phe Thr Leu Lys Ser Asp Val Leu Phe Asn Phe Asn
210                 215                 220 aaa gct acc ctg aaa ccg gaa ggt cag cag gct ctg gat cag ctg tac          720
Lys Ala Thr Leu Lys Pro Glu Gly Gln Gln Ala Leu Asp Gln Leu Tyr
225                 230                 235                 240 act cag ctg agc aac atg gat ccg aaa gac ggt tcc gct gtt gtt ctg          768
Thr Gln Leu Ser Asn Met Asp Pro Lys Asp Gly Ser Ala Val Val Leu
                245                 250                 255 ggc tac acc gac cgc atc ggt tcc gaa gct tac aac cag cag ctg tct          816
Gly Tyr Thr Asp Arg Ile Gly Ser Glu Ala Tyr Asn Gln Gln Leu Ser
            260                 265                 270 gag aaa cgt gct cag tcc gtt gtt gac tac ctg gtt gct aaa ggc atc          864
Glu Lys Arg Ala Gln Ser Val Val Asp Tyr Leu Val Ala Lys Gly Ile
        275                 280                 285 ccg gct ggc aaa atc tcc gct cgc ggc atg ggt gaa tcc aac ccg gtt          912
Pro Ala Gly Lys Ile Ser Ala Arg Gly Met Gly Glu Ser Asn Pro Val
290                 295                 300 act ggc aac acc tgt gac aac gtg aaa gct cgc gct gcc ctg atc gat          960
Thr Gly Asn Thr Cys Asp Asn Val Lys Ala Arg Ala Ala Leu Ile Asp
305                 310                 315                 320 tgc ctg gct ccg gat cgt cgt gta gag atc gaa gtt aaa ggc tac aaa         1008
Cys Leu Ala Pro Asp Arg Arg Val Glu Ile Glu Val Lys Gly Tyr Lys
                325                 330                 335 gaa gtt gta act cag ccg gcg ggt taa                                     1035
Glu Val Val Thr Gln Pro Ala Gly
            340

<210> SEQ ID NO 2
<211> LENGTH: 344
<212> TYPE: PRT
<213> ORGANISM: Klebsiella pneumoniae

<400> SEQUENCE: 2

Met Lys Ala Ile Phe Val Leu Asn Ala Ala Pro Lys Asp Asn Thr Trp
1               5                   10                  15

Tyr Ala Gly Gly Lys Leu Gly Trp Ser Gln Tyr His Asp Thr Gly Phe
            20                  25                  30

Tyr Gly Asn Gly Phe Gln Asn Asn Asn Gly Pro Thr Arg Asn Asp Gln
        35                  40                  45
```

```
Leu Gly Ala Gly Ala Phe Gly Gly Tyr Gln Val Asn Pro Tyr Leu Gly
 50                  55                  60
Phe Glu Met Gly Tyr Asp Trp Leu Gly Arg Met Ala Tyr Lys Gly Ser
 65                  70                  75                  80
Val Asp Asn Gly Ala Phe Lys Ala Gln Gly Val Gln Leu Thr Ala Lys
                 85                  90                  95
Leu Gly Tyr Pro Ile Thr Asp Leu Asp Ile Tyr Thr Arg Leu Gly
            100                 105                 110
Gly Met Val Trp Arg Ala Asp Ser Lys Gly Asn Tyr Ala Ser Thr Gly
        115                 120                 125
Val Ser Arg Ser Glu His Asp Thr Gly Val Ser Pro Val Phe Ala Gly
    130                 135                 140
Gly Val Glu Trp Ala Val Thr Arg Asp Ile Ala Thr Arg Leu Glu Tyr
145                 150                 155                 160
Gln Trp Val Asn Asn Ile Gly Asp Ala Gly Thr Val Gly Thr Arg Pro
                    165                 170                 175
Asp Asn Gly Met Leu Ser Leu Gly Val Ser Tyr Arg Phe Gly Gln Glu
                180                 185                 190
Asp Ala Ala Pro Val Val Ala Pro Ala Pro Ala Pro Ala Pro Glu Val
            195                 200                 205
Ala Thr Lys His Phe Thr Leu Lys Ser Asp Val Leu Phe Asn Phe Asn
        210                 215                 220
Lys Ala Thr Leu Lys Pro Glu Gly Gln Gln Ala Leu Asp Gln Leu Tyr
225                 230                 235                 240
Thr Gln Leu Ser Asn Met Asp Pro Lys Asp Gly Ser Ala Val Val Leu
                245                 250                 255
Gly Tyr Thr Asp Arg Ile Gly Ser Glu Ala Tyr Asn Gln Gln Leu Ser
                260                 265                 270
Glu Lys Arg Ala Gln Ser Val Val Asp Tyr Leu Val Ala Lys Gly Ile
            275                 280                 285
Pro Ala Gly Lys Ile Ser Ala Arg Gly Met Gly Glu Ser Asn Pro Val
        290                 295                 300
Thr Gly Asn Thr Cys Asp Asn Val Lys Ala Arg Ala Ala Leu Ile Asp
305                 310                 315                 320
Cys Leu Ala Pro Asp Arg Arg Val Glu Ile Glu Val Lys Gly Tyr Lys
                325                 330                 335
Glu Val Val Thr Gln Pro Ala Gly
            340

<210> SEQ ID NO 3
<211> LENGTH: 303
<212> TYPE: DNA
<213> ORGANISM: Klebsiella pneumoniae
<220> FEATURE:
<221> NAME/KEY: CDS
<222> LOCATION: (1)..(303)

<400> SEQUENCE: 3 acc gtg aaa acc aaa aac acc acg acc acc cag acc cag ccg agc aaa     48
Thr Val Lys Thr Lys Asn Thr Thr Thr Thr Gln Thr Gln Pro Ser Lys
 1               5                  10                  15 ccg acc acc aaa cag cgt cag aac aaa ccg aac aaa ccg aac aac         96
Pro Thr Thr Lys Gln Arg Gln Asn Lys Pro Asn Lys Pro Asn Asn
             20                  25                  30 gat ttc cat ttc gaa gtg ttc aac ttc gtg ccg tgc agc atc tgc agc    144
Asp Phe His Phe Glu Val Phe Asn Phe Val Pro Cys Ser Ile Cys Ser
```

-continued

```
                35                    40                    45
aac aac ccg acc tgc tgg gcg atc tgc aaa cgt atc ccg aac aaa aaa          192
Asn Asn Pro Thr Cys Trp Ala Ile Cys Lys Arg Ile Pro Asn Lys Lys
        50                    55                    60 ccg ggc aaa aaa acc acg acc aaa ccg acc aaa aaa ccg acc ttc aaa          240
Pro Gly Lys Lys Thr Thr Thr Lys Pro Thr Lys Lys Pro Thr Phe Lys
 65                    70                    75                    80 acc acc aaa aaa gat cat aaa ccg cag acc acc aaa ccg aaa gaa gtg          288
Thr Thr Lys Lys Asp His Lys Pro Gln Thr Thr Lys Pro Lys Glu Val
                85                    90                    95 ccg acc acc aaa ccg                                                      303
Pro Thr Thr Lys Pro
            100

<210> SEQ ID NO 4
<211> LENGTH: 101
<212> TYPE: PRT
<213> ORGANISM: Klebsiella pneumoniae

<400> SEQUENCE: 4

Thr Val Lys Thr Lys Asn Thr Thr Thr Gln Thr Gln Pro Ser Lys
 1               5                   10                  15

Pro Thr Thr Lys Gln Arg Gln Asn Lys Pro Pro Asn Lys Pro Asn Asn
                20                  25                  30

Asp Phe His Phe Glu Val Phe Asn Phe Val Pro Cys Ser Ile Cys Ser
            35                  40                  45

Asn Asn Pro Thr Cys Trp Ala Ile Cys Lys Arg Ile Pro Asn Lys Lys
        50                  55                  60

Pro Gly Lys Lys Thr Thr Thr Lys Pro Thr Lys Lys Pro Thr Phe Lys
 65                 70                  75                  80

Thr Thr Lys Lys Asp His Lys Pro Gln Thr Thr Lys Pro Lys Glu Val
                85                  90                  95

Pro Thr Thr Lys Pro
            100
```